(12) United States Patent
Herzog

(10) Patent No.: US 6,689,585 B1
(45) Date of Patent: Feb. 10, 2004

(54) GABA-B2 RECEPTOR

(75) Inventor: Herbert Herzog, Bondi (AU)

(73) Assignee: The Garvan Institute of Medical Research, New South Wales (AU)

( * ) Notice: Subject to any disclaimer, the term of this patent is extended or adjusted under 35 U.S.C. 154(b) by 0 days.

(21) Appl. No.: 09/719,085

(22) PCT Filed: Jun. 29, 1999

(86) PCT No.: PCT/AU99/00524

§ 371 (c)(1),
(2), (4) Date: Dec. 8, 2000

(87) PCT Pub. No.: WO00/00602

PCT Pub. Date: Jan. 6, 2000

(30) Foreign Application Priority Data

Jun. 29, 1998 (AU) ............................................. PP 4384

(51) Int. Cl.⁷ ............................................... C12N 15/00
(52) U.S. Cl. ................... 435/69.1; 435/320.1; 435/325; 435/252.3; 435/6; 530/350; 536/23.5
(58) Field of Search ............................ 435/69.1, 320.1, 435/252.3, 325, 6; 530/350

(56) References Cited

PUBLICATIONS

Nature 396: 679–682 (1998) by White JH et al. "Heterodimerizationis required for the formation of a functional GABA(B) receptor".

EMBL accession No. AF095784 submitted May 17, 1999 by Lui M et al.
EMBL accession No. AF069755 submitted Jan. 4, 1999 by Ng Gyk et al.
EMBL accesion No. AJ012188 submitted Oct. 16, 1998 by Fraser NJ.
Gen Pept accession No. CAA09942 submitted Oct. 16, 1998 by White JH et al.
EMBL accession No. AF074483 submitted Jun. 25, 1998 by Borowsky B et al.
EMBL accession No. AF056085 submitted Mar. 27, 1998 by Clark JC et al.
Current Opinion In Neurobiology 8(3):345–50 (Jun., 1998) by Bettler B et al. "$GABA_B$ receptors:drugs meet clones."
White et al. Heterodimerization is required for the formation of a functional GABA B receptor. Dec. 1998. Nature, 396:679–682.*
White et al. Locus HSA0121188, GenEmbl, Apr. 29, 1999. Accessed Apr. 24, 2002 (see attached computer printout).*

* cited by examiner

*Primary Examiner*—Lorraine Spector
*Assistant Examiner*—Dong Jiang
(74) *Attorney, Agent, or Firm*—Clark & Brody

(57) ABSTRACT

The invention provides isolated polynucleotide molecules encoding a novel neuropeptide GABA-B receptor (designated GABA-B). These isolated polynucleotide molecules can be used to express the receptor in cells which can then be used to screen compounds for agonist and antagonist activity.

16 Claims, 5 Drawing Sheets

FIGURE 1-1

```
                                                                          70
         *        *        *        *        *        *        *
GAATTCCGACGGGCGGTGTGTACAAAGGGCAGGGACTTAATCAACGCAAGCTTATGACCCGCACTCCTTG
                                                                         140
         *        *        *        *        *        *        *
GCGCGGGGCGGCGGGCCGGGCCAGGCCATGCGGGCCGAGTGAGCCGGCGCCCGCAGCCCGCGGCGCGGCA
                                                                         210
         *        *        *        *        *        *        *
TGGCTTCCCCGCGGAGCTCCGGGCAGCCCGGGCCGCCGCCGCCGCCACCGCCGCCCGCGCGCCTGCT
  M  A  S  P  R  S  S  G  Q  P  G  P  P  P  P  P  P  P  P  A  R  L  L
                                                                         280
         *        *        *        *        *        *        *
ACTGCTACTGCTGCTGCCGCTGCTGCTGCCTCTGGCGCCCGGGGCCTGGGGCTGGGCGCGGGGCGCCCCC
  L  L  L  L  L  P  L  L  L  P  L  A  P  G  A  W  G  W  A  R  G  A  P
                                                                         350
         *        *        *        *        *        *        *
CGGCCGCCGCCCAGCAGCCCGCCGCTCTCCATCATGGGCCTCATGCCGCTCACCAAGGAGGTGGCCAAGG
  R  P  P  P  S  S  P  P  L  S  I  M  G  L  M  P  L  T  K  E  V  A  K
                                                                         420
         *        *        *        *        *        *        *
GCAGCATCGGGCGCGGTGTGCTCCCCGCCGTGGAACTGGCCATCGAGCAGATCCGCAACGAGTCACTCCT
  G  S  I  G  R  G  V  L  P  A  V  E  L  A  I  E  Q  I  R  N  E  S  L  L
                                                                         490
         *        *        *        *        *        *        *
GCGCCCCTACTTCCTCGACCTGCGGCTCTATGACACGGAGTGCGACAACGCAAAAGGGTTGAAAGCCTTC
  R  P  Y  F  L  D  L  R  L  Y  D  T  E  C  D  N  A  K  G  L  K  A  F
                                                                         560
         *        *        *        *        *        *        *
TACGATGCGATAAAATACGGGCCGAACCACTTGATGGTGTTTGGAGGCGTCTGTCCATCCGTCACATCCA
  Y  D  A  I  K  Y  G  P  N  H  L  M  V  F  G  G  V  C  P  S  V  T  S
                                                                         630
         *        *        *        *        *        *        *
TCATTGCAGAGTCCCTCCAAGGCTGGAATCTGGTGCAGCTTTCTTTTGCTGCAACCACGCCTGTTCTAGC
  I  I  A  E  S  L  Q  G  W  N  L  V  Q  L  S  F  A  A  T  T  P  V  L  A
                                                                         700
         *        *        *        *        *        *        *
CGATAAGAAAAAATACCCTTATTTCTTTCGGACCGTCCCATCAGACAATGCGGTGAATCCAGCCATTCTG
  D  K  K  K  Y  P  Y  F  F  R  T  V  P  S  D  N  A  V  N  P  A  I  L
                                                                         770
         *        *        *        *        *        *        *
AAGTTGCTCAAGCACTACCAGTGGAAGCGCGTGGGCACGCTGACGCAAGACGTTCAGAGGTTCTCTGAGG
  K  L  L  K  H  Y  Q  W  K  R  V  G  T  L  T  Q  D  V  Q  R  F  S  E
                                                                         840
         *        *        *        *        *        *        *
TGCGGAATGACCTGACTGGAGTTCTGTATGGCGAGGACATTGAGATTTCAGACACCGAGAGCTTCTCCAA
  V  R  N  D  L  T  G  V  L  Y  G  E  D  I  E  I  S  D  T  E  S  F  S  N
                                                                         910
         *        *        *        *        *        *        *
CGATCCCTGTACCAGTGTCAAAAAGCTGAAGGGGAATGATGTGCGGATCATCCTTGGCCAGTTTGACCAG
  D  P  C  T  S  V  K  K  L  K  G  N  D  V  R  I  I  L  G  Q  F  D  Q
```

FIGURE 1-2

```
                                                                        980
         *         *         *         *         *         *         *
AATATGGCAGCAAAAGTGTTCTGTTGTGCATACGAGGAGAACATGTATGGTAGTAAATATCAGTGGATCA
 N  M  A  A  K  V  F  C  C  A  Y  E  E  N  M  Y  G  S  K  Y  Q  W  I

1050
         *         *         *         *         *         *         *
TTCCGGGCTGGTACGAGCCTTCTTGGTGGGAGCAGGTGCACACGGAAGCCAACTCATCCCGCTGCCTCCG
 I  P  G  W  Y  E  P  S  W  W  E  Q  V  H  T  E  A  N  S  S  R  C  L  R

1120
         *         *         *         *         *         *         *
GAAGAATCTGCTTGCTGCCATGGAGGGCTACATTGGCGTGGATTTCGAGCCCCTGAGCTCCAAGCAGATC
  K  N  L  L  A  A  M  E  G  Y  I  G  V  D  F  E  P  L  S  S  K  Q  I

1190
         *         *         *         *         *         *         *
AAGACCATCTCAGGAAAGACTCCACAGCAGTATGAGAGAGAGTACAACAACAAGCGGTCAGGCGTGGGGC
  K  T  I  S  G  K  T  P  Q  Q  Y  E  R  E  Y  N  N  K  R  S  G  V  G

1260
         *         *         *         *         *         *         *
CCAGCAAGTTCCACGGGTACGCCTACGATGGCATCTGGGTCATCGCCAAGACACTGCAGAGGGCCATGGA
 P  S  K  F  H  G  Y  A  Y  D  G  I  W  V  I  A  K  T  L  Q  R  A  M  E

1330
         *         *         *         *         *         *         *
GACACTGCATGCCAGCAGCCGGCACCAGCGGATCCAGGACTTCAACTACACGGACCACACGCTGGGCAGG
  T  L  H  A  S  S  R  H  Q  R  I  Q  D  F  N  Y  T  D  H  T  L  G  R

1400
         *         *         *         *         *         *         *
ATCATCCTCAATGCCATGAACGAGACCAACTTCTTCGGGGTCACGGGTCAAGTTGTATTCCGGAATGGGG
 I  I  L  N  A  M  N  E  T  N  F  F  G  V  T  G  Q  V  V  F  R  N  G

1470
         *         *         *         *         *         *         *
AGAGAATGGAGACCATTAAATTTACTCAATTTCAAGACAGCAGGGAGGTGAAGGTGGGAGAGTACAACGC
  E  R  M  E  T  I  K  F  T  Q  F  Q  D  S  R  E  V  K  V  G  E  Y  N  A

1540
         *         *         *         *         *         *         *
TGTGGCCGACACACTGGAGATCATCAATGACACCATCAGGTTCCAAGGGTCCGAACCACCAAAAGACAAG
  V  A  D  T  L  E  I  I  N  D  T  I  R  F  Q  G  S  E  P  P  K  D  K

1610
         *         *         *         *         *         *         *
ACCATCATCCTGGAGCAGCTGCGGAAGATCTCCCTACCTCTCTACAGCATCCTCTCTGCCCTCACCATCC
  T  I  I  L  E  Q  L  R  K  I  S  L  P  L  Y  S  I  L  S  A  L  T  I

1680
         *         *         *         *         *         *         *
TCGGGATGATCATGGCCAGTGCTTTTCTCTTCTTCAACATCAAGAACCGGAATCAGAAGCTCATAAAGAT
  L  G  M  I  M  A  S  A  F  L  F  F  N  I  K  N  R  N  Q  K  L  I  K  M

1750
         *         *         *         *         *         *         *
GTCGAGTCCATACATGAACAACCTTATCATCCTTGGAGGGATGCTCTCCTATGCTTCCATATTTCTCTTT
    S  S  P  Y  M  N  N  L  I  I  L  G  G  M  L  S  Y  A  S  I  F  L  F
```

FIGURE 1-3

```
                                                                         1820
       *         *         *         *         *         *         *
GGCCTTGATGGATCCTTTGTCTCTGAAAAGACCTTTGAAACACTTTGCACCGTCAGGACCTGGATTCTCA
 G  L  D  G  S  F  V  S  E  K  T  F  E  T  L  C  T  V  R  T  W  I  L

1890
       *         *         *         *         *         *         *
CCGTGGGCTACACGACCGCTTTTGGGGCCATGTTTGCAAAGACCTGGAGAGTCCACGCCATCTTCAAAAA
 T  V  G  Y  T  T  A  F  G  A  M  F  A  K  T  W  R  V  H  A  I  F  K  N

1960
       *         *         *         *         *         *         *
TGTGAAAATGAAGAAGAAGATCATCAAGGACCAGAAACTGCTTGTGATCGTGGGGGGCATGCTGCTGATC
 V  K  M  K  K  K  I  I  K  D  Q  K  L  L  V  I  V  G  M  L  L  I

2030
       *         *         *         *         *         *         *
GACCTGTGTATCCTGATCTGCTGGCAGGCTGTGGACCCCCTGCGAAGGACAGTGGAGAAGTACAGCATGG
 D  L  C  I  L  I  C  W  Q  A  V  D  P  L  R  R  T  V  E  K  Y  S  M

2100
       *         *         *         *         *         *         *
AGCCGGACCCAGCAGGACGGGATATCTCCATCCGCCCTCTCCTGGAGCACTGTGAGAACACCCATATGAC
 E  P  D  P  A  G  R  D  I  S  I  R  P  L  L  E  H  C  E  N  T  H  M  T

2170
       *         *         *         *         *         *         *
CATCTGGCTTGGCATCGTCTATGCCTACAAGGGACTTCTCATGTTGTTCGGTTGTTTCTTAGCTTGGGAG
  I  W  L  G  I  V  Y  A  Y  K  G  L  L  M  L  F  G  C  F  L  A  W  E

2240
       *         *         *         *         *         *         *
ACCCGCAACGTCAGCATCCCCGCACTCAACGACAGCAAGTACATCGGGATGAGTGTCTACAACGTGGGGA
 T  R  N  V  S  I  P  A  L  N  D  S  K  Y  I  G  M  S  V  Y  N  V  G

2310
       *         *         *         *         *         *         *
TCATGTGCATCATCGGGGCCGCTGTCTCCTTCCTGACCCGGGACCAGCCCAATGTGCAGTTCTGCATCGT
 I  M  C  I  I  G  A  A  V  S  F  L  T  R  D  Q  P  N  V  Q  F  C  I  V

2380
       *         *         *         *         *         *         *
GGCTCTGGTCATCATCTTCTGCAGCACCATCACCCTCTGCCTGGTATTCGTGCCGAAGCTCATCACCCTG
 A  L  V  I  I  F  C  S  T  I  T  L  C  L  V  F  V  P  K  L  I  T  L

2450
       *         *         *         *         *         *         *
AGAACAAACCCAGATGCAGCAACGCAGAACAGGCGATTCCAGTTCACTCAGAATCAGAAGAAAGAAGATT
 R  T  N  P  D  A  A  T  Q  N  R  R  F  Q  F  T  Q  N  Q  K  K  E  D

2520
       *         *         *         *         *         *         *
CTAAAACGTCCACCTCGGTCACCAGTGTGAACCAAGCCAGCACATCCCGCCTGGAGGGCCTACAGTCAGA
 S  K  T  S  T  S  V  T  S  V  N  Q  A  S  T  S  R  L  E  G  L  Q  S  E

2590
       *         *         *         *         *         *         *
AAACCATCGCCTGCGAATGAAGATCACAGAGCTGGATAAAGACTTGGAAGAGGTCACCATGCAGCTGCAG
 N  H  R  L  R  M  K  I  T  E  L  D  K  D  L  E  E  V  T  M  Q  L  Q
```

FIGURE 1-4

```
                                                                                2660
         *         *         *         *         *         *         *
GACACACCAGAAAAGACCACCTACATTAAACAGAACCACTACCAAGAGCTCAATGACATCCTCAACCTGG
 D  T  P  E  K  T  T  Y  I  K  Q  N  H  Y  Q  E  L  N  D  I  L  N  L

2730
         *         *         *         *         *         *         *
GAAACTTCACTGAGAGCACAGATGGAGGAAAGGCCATTTTAAAAAATCACCTCGATCAAAATCCCCAGCT
 G  N  F  T  E  S  T  D  G  G  K  A  I  L  K  N  H  L  D  Q  N  P  Q  L

2800
         *         *         *         *         *         *         *
ACAGTGGAACACAACAGAGCCCTCTCGAACATGCAAAGATCCTATAGAAGATATAAACTCTCCAGAACAC
 Q  W  N  T  T  E  P  S  R  T  C  K  D  P  I  E  D  I  N  S  P  E  H

2870
         *         *         *         *         *         *         *
ATCCAGCGTCGGCTGTCCCTCCAGCTCCCCATCCTCCACCACGCCTACCTCCCATCCATCGGAGGCGTGG
 I  Q  R  R  L  S  L  Q  L  P  I  L  H  H  A  Y  L  P  S  I  G  G  V

2940
         *         *         *         *         *         *         *
ACGCCAGCTGTGTCAGCCCCTGCGTCAGCCCCACCGCCAGCCCCCGCCACAGACATGTGCCACCCTCCTT
 D  A  S  C  V  S  P  C  V  S  P  T  A  S  P  R  H  R  H  V  P  P  S  F

3010
         *         *         *         *         *         *         *
CCGAGTCATGGTCTCGGGCCTGTAAGGGTGGGAGGCCTGGCCCGGGCCTCCCCCGTGACAGAACCACACT
    R  V  M  V  S  G  L

3080
         *         *         *         *         *         *         *
GGGCAGAGGGGTCTGCTGCAGAAACACTGTCGGCTCTGGCTGCGGAGAAGCTGGGCACCATGGCTGGCCT
                                                                                3150
         *         *         *         *         *         *         *
CTCAGGACCACTCGGATGGCACTCAGGTGGACAGGACGGGGCAGGGGGAGACTTGGCACCTGACCTCGAG
                                                                                3220
         *         *         *         *         *         *         *
CCTTATTTGTGAAGTCCTTATTTCTTCACAAAGAAGAGGAACGGAAATGGACGTCTTCCTTAACATCTG
         *         *         *
CAAACAAGGAGGCGCTGGGATATCAAACTGGAATTC
```

FIGURE 2

Sequence alignment of Human GABA-B1b and Human GABA-B2 receptor proteins

```
hGABA-B1b   1  --------MGPGGPCTPVGWP.....LPLLLVM
hGABA-B2    1  MASPRSSGQPGPPPPPPPPPARLLLLLLLPLLLPL hGABA-B1b  21  AAGVAPVWASHSPHLPRPHPRVPPHPSSERRAVYI
hGABA-B2   36  ----APGAWGWARGAPRPPPSSPP.....LSIMGL hGABA-B1b  56  GALFPMSGGWPGGQACQPAVEMALEDVNSRRDILP
hGABA-B2   62  MPLTKEVAKGSIGRGVLPAVELAIEQI-RNESLLR hGABA-B1b  91  DYELKLIHHDSKCDPGQATKYLMELLYNDPIKIIL
hGABA-B2   96  PYFLDLRLYDTECDNAKGLKAFYDAIKYGPNHLMV hGABA-B1b 126  MPG-CSSVSTLVAEAARMWNLIVLSYGSSSPALSN
hGABA-B2  131  FGGVCPSVTSIIAESLQGWNLVQLSFAATTPVLAD hGABA-B1b 160  RQRFPTFFRTHPSATLHNPTRVKLFEKWGWKKIAT
hGABA-B2  166  KKKYPYFFRTVPSDNAVNPAILKLLKHYQWKRVGT hGABA-B1b 195  IQQTTEVFTSTLDDLEERVKEAGIEITFRQSFFSD
hGABA-B2  201  LTQDVQRFSEVRNDLTGVLYGEDLEISDTESFSND hGABA-B1b 230  PAVPVKNLKRQDARIIVGLFYETEARKVFCEVYKE
hGABA-B2  236  PCTSVKKLKGNDVRIILGQFDQNMAAKVFQCAYEE hGABA-B1b 265  RLFGKKYVWFLIGWYADNWFKIYDPSINCTVDEMT
hGABA-B2  271  NMYGSKYQWIIPGWYEPSWWEQVHTEANSSRCLRK hGABA-B1b 300  EAV---EGHITTEIVMLNPANTRSI-SNMTSQEFV
hGABA-B2  306  NLLAAMEGYLGVDFEPLSSKQIKTLSGKTPQQYER hGABA-B1b 331  EKLTKRLKRHPEETGGFQEAPLAYDAIWALALALN
hGABA-B2  341  EYNNKRSGVGPSKFHGY----AYDGLWVIAKTLQ hGABA-B1b 366  KTSGGGGRS--GVRLEDFNYNNQIITDQIYRAMNS
hGABA-B2  371  RAMETLHASSRHQRIQDFNYTDHILGRILLNAMNE hGABA-B1b 399  SSFEGVSGHVVFDASGSRMAWTLIEQPQGGSYKRI
hGABA-B2  406  TNFFGVTGQVVF-RNGERMETIKFTQFQDSREVKV hGABA-B1b 434  GYYDSTKDDLS-WSKTDKWIGGSPPADQTLVIKTF
hGABA-B2  440  GEYNAVADTLEIINDTIRFQGSEPPKDKTIILEQL hGABA-B1b 468  RFLSQKLFISVSVLSSLGIVLAVVCLSFNIYNSHV
hGABA-B2  475  RKISLPLYSILSALTILGMIMASAFLFFNIKNRNQ hGABA-B1b 503  RYIQNSQPNLNNLTAVGCSLALAAVFPLGLDGYHI
hGABA-B2  510  KLLKMSSPYMNNLIILGGMLSYASIFLFGLDGSFV hGABA-B1b 538  GRNQFPFVCQARLWLLGLGFSLGYGSMFTKIWWVH
hGABA-B2  545  SEKTFETLCTVRTWILTVGYTTAFGAMFAKTWRVH hGABA-B1b 573  TGFTKKEEKKEWRKTLEPWKLYATVGLLVGMDVLT
hGABA-B2  580  AIFKNVKMKKKIIK---DQKLLVIVGGMLLIDLCI hGABA-B1b 608  LAIWQIVDPLHRTIETFAKEEPKEDIDVSILPQLE
hGABA-B2  612  LICWQAVDPLRRTVEKYSMEPDPAGRDISIRPLLE hGABA-B1b 643  HCSSRKMNTWLGIFYGYKGLLLLLGIFLAYETKSV
hGABA-B2  647  HCENTHMTIWLGIVYAYKGLLMLFGCFLAWETRNV hGABA-B1b 678  STEKINDHRAVGMAIYNVAVLCLITAPVTMILSSQ
hGABA-B2  682  SIPALNDSKYIGMSVYNYGIMCIIGAAVSFLTRDQ hGABA-B1b 713  QDAAFAFASLAIVFSSYITLVVLFVPKMRRLITRG
hGABA-B2  717  PNVQFCIVALVIIFCSTLTLCLVFVPK---LITLR hGABA-B1b 748  EWQSEAQDTMKTGSSTNNNEEEKSRLLEKENRELE
hGABA-B2  749  TNPDAATQNRRFQFTQNQKKEDSKTSTSVTSVNQA hGABA-B1b 783  KIIAEKEERVSELRHQLQSRQQLRSRRHPPTPPEP
hGABA-B2  784  STSRLEGLQSENHRLRMKITELDKDLEEVTMQLQD hGABA-B1b 818  SGGLPRGPPEPPDRLSCDGSRVHLLYK
hGABA-B2  819  TPEKTTYIKQNHYQELNDILNLGNFTESTDGGKAI hGABA-B2  854  LKNHLDQNPQLQWNTTEPSRTCKDPIEDINSPEHI
hGABA-B2  889  QRRLSLQLPILHHAYLPSIGGVDASCVSPCVSPTA
hGABA-B2  924  SPRHRHVPPSFRVMVSGL
```

GABA-B2 RECEPTOR

FIELD OF THE INVENTION

The present invention relates to isolated polynucleotide molecules which encode a novel transmembrane G-protein coupled receptor designated GABA-B2. The novel receptor appears to be activated by the neurotransmitter γ-amino butyric acid (GABA).

BACKGROUND OF THE INVENTION

γ-amino butyric acid (GABA) is the principal inhibitory neurotransmitter in the brain, whose action is mediated by two types of receptors, GABA-A and GABA-B. GABAergic inhibitory neurons typically form short pathways (e.g. from striatum to substantia nigra and from cerebellar cortex to deep cerebellar nuclei), although at least one long pathway projecting from the posterior hypothalamus to the cerebral cortex has also been recognized. This long pathway is believed to provide a direct pathway by which limbic, emotional and visceral information may be transferred to the cortex (Vincent et al., *Science* 220: 1309–1311, 1993).

GABA-B receptors, such as the GABA-B1*a* and GABA-B1*b* receptors, are predominantly present in the brain where they are believed to play a major role in learning and memory. In view of these functions and the known benefit of GABA-B agonists (e.g. baclofen) in the treatment of spasticity, anxiety and depression, there is considerable interest in isolating genes encoding GABA-B receptor subtypes so as to, enable the recombinant production of GABA-B receptors for the development of novel therapeutics.

SUMMARY OF THE INVENTION

In a first aspect, the present invention provides an isolated polyniucleotide molecule encoding a GABA-B2 receptor or a functionally equivalent fragment thereof.

Preferably, the encoded GABA-B2 receptor is characterised by the N-terminal amino acid sequence: MASPRSS-GQP (SEQ ID NO: 1)

More preferably, the isolated polynucleotide molecule encodes a human GABA-B2 receptor of about 941 amino acids.

Most preferably, the isolated polynucleotide molecule encodes a GABA-B2 receptor having an amino acid sequence substantially corresponding to that shown as SEQ ID NO: 2.

The polynucleotide molecule of the first aspect may comprise a nucleotide sequence substantially corresponding to, or showing at least 90% (more preferably, at least 95%) homology to that shown at nucleotides 1 to 3256 or nucleotides 140 to 2962 of SEQ ID NO: 3 or any portion thereof encoding a functionally equivalent GABA-B2 receptor fragment.

The isolated polynucleotide molecule may be incorporated into plasmids or expression vectors (including viral vectors), which may then be introduced into suitable bacterial, yeast, insect and mammalian host cells. Such host cells may be used to express the GABA-B2 receptor encoded by the isolated polynucleotide molecule.

Accordingly, in a second aspect, the present invention provides a mammalian, insect, yeast or bacterial host cell transformed with the polynucleotide molecule of the first aspect.

In a third aspect, the present invention provides a method of producing GABA-B2 receptors or functionally equivalent fragments thereof, comprising culturing the host cell of the second aspect under conditions enabling the expression of GABA-B2 receptors or functionally equivalent fragments thereof.

Preferably, the host cell is mammalian or of insect origin. Where the cell is mammalian, it is presently preferred that it be a Chinese hamster ovary (CHO) cell, monkey kidney (COS) cell or human embryonic kidney 293 cell. Where the cell is of insect origin, it is presently preferred that it be an insect Sf9 cell.

In a preferred embodiment, the GABA-B2 receptors or fragments thereof are expressed onto the surface of the host cell.

By using the polynucleotide molecule of the present invention it is possible to obtain GABA-B2 receptor protein or fragments thereof in a substantially pure form.

Accordingly, in a fourth aspect, the present invention provides a GABA-B2 receptor or a functionally equivalent fragment of said receptor, in a substantially pure form.

In a fifth aspect, the present invention provides an antibody capable of specifically binding to the GABA-B2 receptor of the fourth aspect. Such antibodies may be produced by any of the methods routine to the art.

In a sixth aspect, the present invention provides a non-human animal transformed with a polyniucleotide molecule according to the first aspect of the present invention.

In a seventh aspect, the present invention provides a method for detecting agonist or antagonist agents of a GABA-B2 receptor, comprising contacting a GABA-B2 receptor, functionally equivalent fragment thereof or a cell transfected with and expressing the polynucleotide molecule of the first aspect, with a test agent under conditions enabling the activation of a GABA-B2 receptor, and detecting an increase or decrease in activity of the GABA-B2 receptor or functionally equivalent fragment thereof.

An increase or decrease in activity of the receptor or functionally equivalent fragment thereof may be detected by measuring changes in cAMP production, $Ca^{2+}$ levels or IP3 turnover after activating the receptor molecule with specific agonists or antagonists.

In a further aspect, the present invention provides an oligonucleotide or polynucleotide probe comprising a nucleotide sequence of 10 or more nucleotides, the probe comprising a nucleotide sequence such that the probe specifically hybridises to the polynucleotide molecule of the first aspect under high stringency conditions (Samibrook et al., *Molecular cloning: a laboratory manual*, Second Edition, Cold Spring Harbor Laboratory Press).

In a still further aspect, the present invention provides an antisense oligonucleotide or polynucleotide molecule comprising a nucleotide sequence capable of specifically hybridising to an mRNA molecule which encodes a GABA-B2 receptor so as to prevent translation of the mRNA molecule.

Such antisense oligonucleotide or polynucleotide molecules may include a ribozyme region to catalytically inactivate mRNA to which it is hybridised.

The polynucleotide molecule of the first aspect of the invention may be a dominant negative mutant which encodes a gene product causing an altered phenotype by, for example, reducing or eliminating the activity of endogenous GABA-B2 receptors.

The term "substantially corresponding" as used herein in relation to amino acid sequences is intended to encompass minor variations in the amino acid sequences which do not result in a decrease in biological activity of the GABA-B2 receptor. These variations may include conservative amino acid substitutions. The substitutions envisaged are:

G, A, V, I, L, M; D, E; N, Q; S, T; K, R, H; F, Y, W, H; and P, Nα-alkalamiino acids.

The term "substantially corresponding" as used herein in relation to nucleotide sequences is intended to encompass minor variations in the nucleotide sequences which due to degeneracy in the DNA code do not result in a change in the encoded protein. Further, this term is intended to encompass other minor variations in the sequence which may be required to enhance expression in a particular system but in which the variations do not result in a decrease in biological activity of the encoded protein.

The term "functionally equivalent fragment/s" as used herein is intended to refer to fragments of the GABA-B2 receptor that exhibit binding specificity and activity that is substantially equivalent to the GABA-B2 receptor from which it/they is/are derived.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Reference to percent homology made in this specification have been calculated using the BLAST program blastn as described by Altschul, S. F. et al., "Capped BLAST and PSI-BLAST: a new generation of protein database search programs", *Nucleic Acids Research*, Vol. 25, No. 17, pp. 3389–3402 (1997).

BRIEF DESCRIPTION OF THE ACCOMPANYING FIGURES

FIG. 1 provides the nucleotide sequence of a cDNA encoding the human GABA-B2 receptor and includes the predicted amino acid sequence.

FIG. 2 shows the degree of identity between the predicted amino acid sequence of the human GABA-B2 and GABA-B1b receptors.

DETAILED DISCLOSURE OF THE INVENTION

Human GABA-B2 Receptor cDNA

A human lippocampus cDNA library (Stratagene) was screened under low stringency conditions with a 184 bp $^{32}$P-labelled fragment (corresponding to nucleotides 2051 to 2235 of SEQ ID NO: 3) originated from a human brain EST clone (z43654). A cDNA clone encoding a complete human GABA-B gene was obtained from the screen. The nucleotide sequence of the cDNA clone is shown as SEQ ID NO: 3 and encodes a protein of 941 amino acids (SEQ ID NO: 2) consisting of a large extracellular domain (amino acids 1 to 480) followed by 7 hydrophobic regions (amino acids 481 to 494, 518 to 545, 558 to 578, 597 to 618, 653 to 676, 691 to 713 and 719 to 743) typical of G-protein coupled receptors.

Sequence comparison with other G-protein coupled receptors identify GABA-B1a, GABA-B1b (FIG. 1) and metabotropic glutamate receptors (Kaupinan, K. et al., *Nature* 386: 239–246, Mar. 20, 1997 and Pin, J. et al., *Neuropharmacology* 34: 1–26, 1995) as the most closely related group.

Northern analysis has identified brain as the tissue with the highest expression of the human GABA-B2 mRNA. In particular, Northern analysis experiments using multiple tissue Northern blots (Clontech) identified high levels of expression of the human GABA-B2 mRNA in the cerebellum, cerebral cortex, occipital pole, frontal lobe and temporal lobe. Lower levels of expression were seen in the thalamus, amygldala, hippocampus, substantia nigra, putamen, subthalamic nucleus, caudate nucleus, and medulla. No apparent expression was seen in the spinal cord and corpus callosum.

Further, in situ hybridisation of rat brain sections has identified discrete areas of expression in the hippocampus, amygdala, the piriform cortex and also the hypothalamus. This mRNA distribution is consistent with the expression of other subtypes of the GABA-B receptor family.

Chromosomal Localisation of Human GABA-B2 receptor gene

In order to determine the chromosomal localisation of the human GABA-B2 receptor gene, the complete cDNA clone was nick-translated with biotin-14-dAPT and hybridised in situ at a final concentration of 5 ng/ml to metaphase chromosomal spreads from two normal males. The fluoerescence in situ hybridisation (FISH) method was modified from that previously described (Callen, DF et al., Ann Genet 33: 219–221 1990) in that chromosomes were stained before analysis with both propidium iodide (as counterstain) and DAPI (for chromosome identification). Images of metaphase preparations were captured by a CCD camera and computer enhancement software.

Twenty metaphases from a first normal male were examined for fluorescent signal. All of these metaphases showed signal on one or both chromatids of chromosome 9 in the region 9q21. There was a total of 7 non-specific background dots observed in these 20 metaphases. A similar result was obtained from hybridisation of the probe to 20 metaphases from a second normal male.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An isolated polynucleotide molecule that encodes a GABA-B receptor polypeptide wherein said polynucleotide molecule comprises a nucleotide sequence selected from the group consisting of:
   (i) the sequence set forth in SEQ ID NO; 3;
   (ii) the sequence consisting of nucieotides 140 to 2962 of SEQ ID NO: 3; and
   (iii) a sequence that encodes the amino acid sequence set forth in SEQ ID NO: 2.

2. An isolated polynucleotide molecule according to claim 1, wherein the polynucleotide molecule encodes a GABA-B receptor polypeptide of human origin of 941 amino acids in length.

3. An isolated polynucleotide molecule that encodes a human GABA-B receptor polypeptide having an amino add sequence corresponding to the sequence set forth in SEQ ID NO: 2.

4. An isolated polynucleotide molecule that encodes a GABA-B receptor polypeptide, wherein said polynucleotide molecule comprises a nucleotide sequence consisting of nucleotides 1 to 3256 of SEQ ID NO: 3.

5. An isolated polynucleotide molecule that encodes a GABA-B receptor polypeptide, wherein said polynucleotide molecule comprises a nucleotide sequence consisting of nucleotides 140 to 2962 of SEQ ID NO: 3.

6. A plasmid or expression vector comprising a polynucleotide molecule according to claim 1.

7. A host cell transformed with a polynucleotide molecule according to claim 1.

8. A host cell according to claim 7, wherein the cell is a mammalian or insect cell.

9. A host cell according to claim 8, wherein the cell is a Chinese hamster ovary (CHO) cell, human embryonic kidney (HEK) 293 cell or an insect Sf9 cell.

10. A host cell according to claim 7, wherein the cell expresses on the cell's surface the GABA-B receptor polypeptide encoded by the polynucleotide transformed into the cell.

11. A method of producing a GABA-B receptor polypeptide, said method comprising culturing a host cell transformed with the polynucleotide of claim 1 under conditions sufficient for expression of the GABA-B receptor polypeptide encoded by the polynucleotide to occur.

12. The method of claim 11 further comprising recovering the GABA-B receptor polypeptide from the host cell substantially free of other proteins.

13. A method of producing a GABA-B receptor polypeptide, said method comprising introducing the polynucleotide of claim 1 encoding a GABA-B receptor polypeptide into a cell thereby producing a transformed cell and then growing the transformed cell under conditions sufficient for expression of the encoded GABA-B receptor polypeptide to occur.

14. A GABA-B receptor polypeptide comprising the amino acid sequence set forth In SEQ ID NO: 2, substantially free of other human proteins.

15. A receptor polypeptide according to claim 14, wherein said polypeptide is a human receptor of 941 amino acids.

16. A receptor polypeptide according to claim 14, wherein said receptor has an amino acid sequence corresponding to that shown as SEQ ID NO: 2.

* * * * *

SEQUENCE LISTING

<160> NUMBER OF SEQ ID NOS: 4

<210> SEQ ID NO 1
<211> LENGTH: 10
<212> TYPE: PRT
<213> ORGANISM: Homo sapiens

```
<400> SEQUENCE: 1

Met Ala Ser Pro Arg Ser Ser Gly Gln Pro
  1               5                  10

<210> SEQ ID NO 2
<211> LENGTH: 941
<212> TYPE: PRT
<213> ORGANISM: Homo sapiens

<400> SEQUENCE: 2

Met Ala Ser Pro Arg Ser Ser Gly Gln Pro Gly Pro Pro Pro Pro
  1               5                  10                  15

Pro Pro Pro Pro Ala Arg Leu Leu Leu Leu Leu Leu Pro Leu Leu
                 20                  25                  30

Leu Pro Leu Ala Pro Gly Ala Trp Gly Trp Ala Arg Gly Ala Pro Arg
             35                  40                  45

Pro Pro Pro Ser Ser Pro Leu Ser Ile Met Gly Leu Met Pro Leu
         50                  55                  60

Thr Lys Glu Val Ala Lys Gly Ser Ile Gly Arg Gly Val Leu Pro Ala
 65                  70                  75                  80

Val Glu Leu Ala Ile Glu Gln Ile Arg Asn Glu Ser Leu Leu Arg Pro
                 85                  90                  95

Tyr Phe Leu Asp Leu Arg Leu Tyr Asp Thr Glu Cys Asp Asn Ala Lys
                100                 105                 110

Gly Leu Lys Ala Phe Tyr Asp Ala Ile Lys Tyr Gly Pro Asn His Leu
            115                 120                 125

Met Val Phe Gly Gly Val Cys Pro Ser Val Thr Ser Ile Ile Ala Glu
    130                 135                 140

Ser Leu Gln Gly Trp Asn Leu Val Gln Leu Ser Phe Ala Ala Thr Thr
145                 150                 155                 160

Pro Val Leu Ala Asp Lys Lys Lys Tyr Pro Tyr Phe Phe Arg Thr Val
                165                 170                 175

Pro Ser Asp Asn Ala Val Asn Pro Ala Ile Leu Lys Leu Leu Lys His
            180                 185                 190

Tyr Gln Trp Lys Arg Val Gly Thr Leu Thr Gln Asp Val Gln Arg Phe
        195                 200                 205

Ser Glu Val Arg Asn Asp Leu Thr Gly Val Leu Tyr Gly Glu Asp Ile
    210                 215                 220

Glu Ile Ser Asp Thr Glu Ser Phe Ser Asn Asp Pro Cys Thr Ser Val
225                 230                 235                 240

Lys Lys Leu Lys Gly Asn Asp Val Arg Ile Ile Leu Gly Gln Phe Asp
                245                 250                 255

Gln Asn Met Ala Ala Lys Val Phe Cys Cys Ala Tyr Glu Glu Asn Met
            260                 265                 270

Tyr Gly Ser Lys Tyr Gln Trp Ile Ile Pro Gly Trp Tyr Glu Pro Ser
        275                 280                 285

Trp Trp Glu Gln Val His Thr Gly Ala Asn Ser Ser Arg Cys Leu Arg
    290                 295                 300

Lys Asn Leu Leu Ala Ala Met Glu Gly Tyr Ile Gly Val Asp Phe Glu
305                 310                 315                 320

Pro Leu Ser Ser Lys Gln Ile Lys Thr Ile Ser Gly Lys Thr Pro Gln
                325                 330                 335

Gln Tyr Glu Arg Glu Tyr Asn Asn Lys Arg Ser Gly Val Gly Pro Ser
            340                 345                 350
```

-continued

```
Lys Phe His Gly Tyr Ala Tyr Asp Gly Ile Trp Val Ile Ala Lys Thr
        355                 360                 365
Leu Gln Arg Ala Met Glu Thr Leu His Ala Ser Ser Arg His Gln Arg
    370                 375                 380
Ile Gln Asp Phe Asn Tyr Thr Asp His Thr Leu Gly Arg Ile Ile Leu
385                 390                 395                 400
Asn Ala Met Asn Glu Thr Asn Phe Phe Gly Val Thr Gly Gln Val Val
                405                 410                 415
Phe Arg Asn Gly Glu Arg Met Glu Thr Ile Lys Phe Thr Gln Phe Gln
            420                 425                 430
Asp Ser Arg Glu Val Lys Val Gly Glu Tyr Asn Ala Val Ala Asp Thr
        435                 440                 445
Leu Glu Ile Ile Asn Asp Thr Ile Arg Phe Gln Gly Ser Glu Pro Pro
    450                 455                 460
Lys Asp Lys Thr Ile Ile Leu Glu Gln Leu Arg Lys Ile Ser Leu Pro
465                 470                 475                 480
Leu Tyr Ser Ile Leu Ser Ala Leu Thr Ile Leu Gly Met Ile Met Ala
                485                 490                 495
Ser Ala Phe Leu Phe Phe Asn Ile Lys Asn Arg Asn Gln Lys Leu Ile
            500                 505                 510
Lys Met Ser Ser Pro Tyr Met Asn Asn Leu Ile Ile Leu Gly Gly Met
        515                 520                 525
Leu Ser Tyr Ala Ser Ile Phe Leu Phe Gly Leu Asp Gly Ser Phe Val
    530                 535                 540
Ser Glu Lys Thr Phe Glu Thr Leu Cys Thr Val Arg Thr Trp Ile Leu
545                 550                 555                 560
Thr Val Gly Tyr Thr Thr Ala Phe Gly Ala Met Phe Ala Lys Thr Trp
                565                 570                 575
Arg Val His Ala Ile Phe Lys Asn Val Lys Met Lys Lys Lys Ile Ile
            580                 585                 590
Lys Asp Gln Lys Leu Leu Val Ile Val Gly Gly Met Leu Leu Ile Asp
        595                 600                 605
Leu Cys Ile Leu Ile Cys Trp Gln Ala Val Asp Pro Leu Arg Arg Thr
    610                 615                 620
Val Glu Lys Tyr Ser Met Glu Pro Asp Pro Ala Gly Arg Asp Ile Ser
625                 630                 635                 640
Ile Arg Pro Leu Leu Glu His Cys Glu Asn Thr His Met Thr Ile Trp
                645                 650                 655
Leu Gly Ile Val Tyr Ala Tyr Lys Gly Leu Leu Met Leu Phe Gly Cys
            660                 665                 670
Phe Leu Ala Trp Glu Thr Arg Asn Val Ser Ile Pro Ala Leu Asn Asp
        675                 680                 685
Ser Lys Tyr Ile Gly Met Ser Val Tyr Asn Val Gly Ile Met Cys Ile
    690                 695                 700
Ile Gly Ala Ala Val Ser Phe Leu Thr Arg Asp Gln Pro Asn Val Gln
705                 710                 715                 720
Phe Cys Ile Val Ala Leu Val Ile Phe Cys Ser Thr Ile Thr Leu
                725                 730                 735
Cys Leu Val Phe Val Pro Lys Leu Ile Thr Leu Arg Thr Asn Pro Asp
            740                 745                 750
Ala Ala Thr Gln Asn Arg Arg Phe Gln Phe Thr Gln Asn Gln Lys Lys
        755                 760                 765
```

| | | | | | | | | | | | | |
|---|---|---|---|---|---|---|---|---|---|---|---|---|
|Glu|Asp|Ser|Lys|Thr|Ser|Thr|Ser|Val|Thr|Ser|Val|Asn|Gln|Ala|Ser|
| |770| | | |775| | | |780| | | | | | |

Thr Ser Arg Leu Glu Gly Leu Gln Ser Glu Asn His Arg Leu Arg Met
785               790               795               800

Lys Ile Thr Glu Leu Asp Lys Asp Leu Glu Glu Val Thr Met Gln Leu
                805               810               815

Gln Asp Thr Pro Glu Lys Thr Thr Tyr Ile Lys Gln Asn His Tyr Gln
            820               825               830

Glu Leu Asn Asp Ile Leu Asn Leu Gly Asn Phe Thr Glu Ser Thr Asp
            835               840               845

Gly Gly Lys Ala Ile Leu Lys Asn His Leu Asp Gln Asn Pro Gln Leu
    850               855               860

Gln Trp Asn Thr Thr Glu Pro Ser Arg Thr Cys Lys Asp Pro Ile Glu
865               870               875               880

Asp Ile Asn Ser Pro Glu His Ile Gln Arg Arg Leu Ser Leu Gln Leu
            885               890               895

Pro Ile Leu His His Ala Tyr Leu Pro Ser Ile Gly Gly Val Asp Ala
            900               905               910

Ser Cys Val Ser Pro Cys Val Ser Pro Thr Ala Ser Pro Arg His Arg
        915               920               925

His Val Pro Pro Ser Phe Arg Val Met Val Ser Gly Leu
    930               935               940

<210> SEQ ID NO 3
<211> LENGTH: 3256
<212> TYPE: DNA
<213> ORGANISM: Homo sapiens

<400> SEQUENCE: 3

| | | | | |
|---|---|---|---|---|
|gaattccgac gggcggtgtg tacaaagggc agggacttaa tcaacgcaag cttatgaccc|60|
|gcactccttg gcgcggggcg gcgggccggg ccaggccatg cgggccgagt gagccggcgc|120|
|ccgcagcccg cggcgcggca tggcttcccc gcggagctcc gggcagcccg ggccgccgcc|180|
|gccgccgcca ccgccgcccg cgcgcctgct actgctactg ctgctgccgc tgctgctgcc|240|
|tctggcgccc ggggcctggg gctgggcgcg gggcgccccc cggccgccgc ccagcagccc|300|
|gccgctctcc atcatgggcc tcatgccgct caccaaggag gtggccaagg gcagcatcgg|360|
|gcgcggtgtg ctccccgccg tggaactggc catcgagcag atccgcaacg agtcactcct|420|
|gcgcccctac ttcctcgacc tgcggctcta tgacacggag tgcgacaacg caaaagggtt|480|
|gaaagccttc tacgatgcga taaaatacgg gccgaaccac ttgatggtgt ttggaggcgt|540|
|ctgtccatcc gtcacatcca tcattgcaga gtccctccaa ggctggaatc tggtgcagct|600|
|ttcttttgct gcaaccacgc ctgttctagc cgataagaaa aaatacccta tttctttcg|660|
|gaccgtccca tcagacaatg cggtgaatcc agccattctg aagttgctca agcactacca|720|
|gtggaagcgc gtgggcacgc tgacgcaaga cgttcagagg ttctctgagg tgcggaatga|780|
|cctgactgga gttctgtatg cgaggacat tgagatttca gacaccgaga gcttctccaa|840|
|cgatccctgt accagtgtca aaaagctgaa ggggaatgat gtgcggatca tccttggcca|900|
|gtttgaccag aatatggcag caaaagtgtt ctgttgtgca tacgaggaga acatgtatgg|960|
|tagtaaatat cagtggatca ttccgggctg gtacgagcct tcttggtggg agcaggtgca|1020|
|cacggaagcc aactcatccc gctgcctccg gaagaatctg cttgctgcca tggagggcta|1080|
|cattggcgtg gatttcgagc ccctgagctc caagcagatc aagaccatct caggaaagac|1140|

```
tccacagcag tatgagagag agtacaacaa caagcggtca ggcgtggggc ccagcaagtt    1200
ccacgggtac gcctacgatg gcatctgggt catcgccaag acactgcaga gggccatgga    1260
gacactgcat gccagcagcc ggcaccagcg gatccaggac ttcaactaca cggaccacac    1320
gctgggcagg atcatcctca atgccatgaa cgagaccaac ttcttcgggg tcacgggtca    1380
agttgtattc cggaatgggg agagaatgga gaccattaaa tttactcaat ttcaagacag    1440
cagggaggtg aaggtgggag agtacaacgc tgtggccgac acactggaga tcatcaatga    1500
caccatcagg ttccaagggt ccgaaccacc aaaagacaag accatcatcc tggagcagct    1560
gcggaagatc tccctacctc tctacagcat cctctctgcc ctcaccatcc tcgggatgat    1620
catggccagt gcttttctct tcttcaacat caagaaccgg aatcagaagc tcataaagat    1680
gtcgagtcca tacatgaaca accttatcat ccttggaggg atgctctcct atgcttccat    1740
atttctcttt ggccttgatg gatcctttgt ctctgaaaag acctttgaaa cactttgcac    1800
cgtcaggacc tggattctca ccgtgggcta cacgaccgct tttggggcca tgtttgcaaa    1860
gacctggaga gtccacgcca tcttcaaaaa tgtgaaaatg aagaagaaga tcatcaagga    1920
ccagaaactg cttgtgatcg tggggggcat gctgctgatc gacctgtgta tcctgatctg    1980
ctggcaggct gtggaccccc tgcgaaggac agtggagaag tacagcatgg agccggaccc    2040
agcaggacgg gatatctcca tccgccctct cctggagcac tgtgagaaca cccatatgac    2100
catctggctt ggcatcgtct atgcctacaa gggacttctc atgttgttcg gttgtttctt    2160
agcttgggag acccgcaacg tcagcatccc cgcactcaac gacagcaagt acatcgggat    2220
gagtgtctac aacgtgggga tcatgtgcat catcggggcc gctgtctcct tcctgacccg    2280
ggaccagccc aatgtgcagt tctgcatcgt ggctctggtc atcatcttct gcagcaccat    2340
caccctctgc ctggtattcg tgccgaagct catcaccctg agaacaaacc cagatgcagc    2400
aacgcagaac aggcgattcc agttcactca gaatcagaag aaagaagatt ctaaaacgtc    2460
cacctcggtc accagtgtga accaagccag cacatcccgc ctggagggcc tacagtcaga    2520
aaaccatcgc ctgcgaatga agatcacaga gctggataaa gacttggaag aggtcaccat    2580
gcagctgcag gacacaccag aaaagaccac ctacattaaa cagaaccact accaagagct    2640
caatgacatc ctcaacctgg gaaacttcac tgagagcaca gatggaggaa aggccatttt    2700
aaaaaatcac ctcgatcaaa atccccagct acagtgaaac acaacagagc cctctcgaac    2760
atgcaaagat cctatagaag atataaactc tccagaacac atccagcgtc ggctgtccct    2820
ccagctcccc atcctccacc acgcctacct cccatccatc ggaggcgtgg acgccagctg    2880
tgtcagcccc tgcgtcagcc ccaccgccag ccccgccac agacatgtgc caccctcctt    2940
ccgagtcatg gtctcgggcc tgtaagggtg ggaggcctgg cccgggcctc ccccgtgaca    3000
gaaccacact gggcagaggg gtctgctgca gaaacactgt cggctctggc tgcggagaag    3060
ctgggcacca tggctggcct ctcaggacca ctcggatggc actcaggtgg acaggacggg    3120
gcagggggag acttgcacc tgacctcgag ccttatttgt gaagtcctta tttcttcaca    3180
aagaagagga acgaaatgg gacgtcttcc ttaacatctg caaacaagga ggcgctggga    3240
tatcaaactg gaattc                                                    3256
```

<210> SEQ ID NO 4
<211> LENGTH: 844
<212> TYPE: PRT
<213> ORGANISM: Homo sapiens

<400> SEQUENCE: 4

| | | | | | | | | | | | | | | |
|---|---|---|---|---|---|---|---|---|---|---|---|---|---|---|
|Met|Gly|Pro|Gly|Gly|Pro|Cys|Thr|Pro|Val|Gly|Trp|Pro|Leu|Pro|Leu|
|1| | | |5| | | | |10| | | | |15| |

| | | | | | | | | | | | | | | | |
|---|---|---|---|---|---|---|---|---|---|---|---|---|---|---|---|
|Leu|Leu|Val|Met|Ala|Ala|Gly|Val|Ala|Pro|Val|Trp|Ala|Ser|His|Ser|
| | | |20| | | | |25| | | | |30| | |

Pro His Leu Pro Arg Pro His Pro Arg Val Pro Pro His Pro Ser Ser
       35              40              45

Glu Arg Arg Ala Val Tyr Ile Gly Ala Leu Phe Pro Met Ser Gly Gly
 50              55              60

Trp Pro Gly Gly Gln Ala Cys Gln Pro Ala Val Glu Met Ala Leu Glu
 65           70              75              80

Asp Val Asn Ser Arg Arg Asp Ile Leu Pro Asp Tyr Glu Leu Lys Leu
             85              90              95

Ile His His Asp Ser Lys Cys Asp Pro Gly Gln Ala Thr Lys Tyr Leu
             100             105             110

Tyr Glu Leu Leu Tyr Asn Asp Pro Ile Lys Ile Ile Leu Met Pro Gly
         115             120             125

Cys Ser Ser Val Ser Thr Leu Val Ala Glu Ala Arg Met Trp Asn
130             135             140

Leu Ile Val Leu Ser Tyr Gly Ser Ser Pro Ala Leu Ser Asn Arg
145             150             155             160

Gln Arg Phe Pro Thr Phe Phe Arg Thr His Pro Ser Ala Thr Leu His
         165             170             175

Asn Pro Thr Arg Val Lys Leu Phe Glu Lys Trp Gly Trp Lys Lys Ile
         180             185             190

Ala Thr Ile Gln Gln Thr Thr Glu Val Phe Thr Ser Thr Leu Asp Asp
         195             200             205

Leu Glu Glu Arg Val Lys Glu Ala Gly Ile Glu Ile Thr Phe Arg Gln
     210             215             220

Ser Phe Phe Ser Asp Pro Ala Val Pro Val Lys Asn Leu Lys Arg Gln
225             230             235             240

Asp Ala Arg Ile Ile Val Gly Leu Phe Tyr Glu Thr Glu Ala Arg Lys
             245             250             255

Val Phe Cys Glu Val Tyr Lys Glu Arg Leu Phe Gly Lys Lys Tyr Val
         260             265             270

Trp Phe Leu Ile Gly Trp Tyr Ala Asp Asn Trp Phe Lys Ile Tyr Asp
         275             280             285

Pro Ser Ile Asn Cys Thr Val Asp Glu Met Thr Glu Ala Val Glu Gly
     290             295             300

His Ile Thr Thr Glu Ile Val Met Leu Asn Pro Ala Asn Thr Arg Ser
305             310             315             320

Ile Ser Asn Met Thr Ser Gln Glu Phe Val Glu Lys Leu Thr Lys Arg
         325             330             335

Leu Lys Arg His Pro Glu Glu Thr Gly Gly Phe Gln Glu Ala Pro Leu
         340             345             350

Ala Tyr Asp Ala Ile Trp Ala Leu Ala Leu Ala Leu Asn Lys Thr Ser
         355             360             365

Gly Gly Gly Gly Arg Ser Gly Val Arg Leu Glu Asp Phe Asn Tyr Asn
     370             375             380

Asn Gln Thr Ile Thr Asp Gln Ile Tyr Arg Ala Met Asn Ser Ser Ser
385             390             395             400

Phe Glu Gly Val Ser Gly His Val Val Phe Asp Ala Ser Gly Ser Arg
             405             410             415

-continued

```
Met Ala Trp Thr Leu Ile Glu Gln Pro Gln Gly Gly Ser Tyr Lys Lys
                420                 425                 430

Ile Gly Tyr Tyr Asp Ser Thr Lys Asp Asp Leu Ser Trp Ser Lys Thr
            435                 440                 445

Asp Lys Trp Ile Gly Gly Ser Pro Pro Ala Asp Gln Thr Leu Val Ile
450                 455                 460

Lys Thr Phe Arg Phe Leu Ser Gln Lys Leu Phe Ile Ser Val Ser Val
465                 470                 475                 480

Leu Ser Ser Leu Gly Ile Val Leu Ala Val Val Cys Leu Ser Phe Asn
                485                 490                 495

Ile Tyr Asn Ser His Val Arg Tyr Ile Gln Asn Ser Gln Pro Asn Leu
                500                 505                 510

Asn Asn Leu Thr Ala Val Gly Cys Ser Leu Ala Leu Ala Ala Val Phe
            515                 520                 525

Pro Leu Gly Leu Asp Gly Tyr His Ile Gly Arg Asn Gln Phe Pro Phe
530                 535                 540

Val Cys Gln Ala Arg Leu Trp Leu Leu Gly Leu Gly Phe Ser Leu Gly
545                 550                 555                 560

Tyr Gly Ser Met Phe Thr Lys Ile Trp Trp Val His Thr Gly Phe Thr
                565                 570                 575

Lys Lys Glu Glu Lys Lys Glu Trp Arg Lys Thr Leu Glu Pro Trp Lys
                580                 585                 590

Leu Tyr Ala Thr Val Gly Leu Leu Val Gly Met Asp Val Leu Thr Leu
            595                 600                 605

Ala Ile Trp Gln Ile Val Asp Pro Leu His Arg Thr Ile Glu Thr Phe
610                 615                 620

Ala Lys Glu Glu Pro Lys Glu Asp Ile Asp Val Ser Ile Leu Pro Gln
625                 630                 635                 640

Leu Glu His Cys Ser Ser Arg Lys Met Asn Thr Trp Leu Gly Ile Phe
                645                 650                 655

Tyr Gly Tyr Lys Gly Leu Leu Leu Leu Gly Ile Phe Leu Ala Tyr
                660                 665                 670

Glu Thr Lys Ser Val Ser Thr Glu Lys Ile Asn Asp His Arg Ala Val
            675                 680                 685

Gly Met Ala Ile Tyr Asn Val Ala Val Leu Cys Leu Ile Thr Ala Pro
690                 695                 700

Val Thr Met Ile Leu Ser Ser Gln Gln Asp Ala Ala Phe Ala Phe Ala
705                 710                 715                 720

Ser Leu Ala Ile Val Phe Ser Ser Tyr Ile Thr Leu Val Val Leu Phe
                725                 730                 735

Val Pro Lys Met Arg Arg Leu Ile Thr Arg Gly Glu Trp Gln Ser Glu
            740                 745                 750

Ala Gln Asp Thr Met Lys Thr Gly Ser Ser Thr Asn Asn Glu Glu
            755                 760                 765

Glu Lys Ser Arg Leu Leu Glu Lys Glu Asn Arg Glu Leu Glu Lys Ile
            770                 775                 780

Ile Ala Glu Lys Glu Glu Arg Val Ser Glu Leu Arg His Gln Leu Gln
785                 790                 795                 800

Ser Arg Gln Gln Leu Arg Ser Arg Arg His Pro Thr Pro Pro Glu
                805                 810                 815
```

```
-continued

Pro Ser Gly Gly Leu Pro Arg Gly Pro Pro Glu Pro Pro Asp Arg Leu
            820                 825                 830

Ser Cys Asp Gly Ser Arg Val His Leu Leu Tyr Lys
            835                 840
```